(12) United States Patent
Schatz

(10) Patent No.: US 8,414,558 B2
(45) Date of Patent: Apr. 9, 2013

(54) MYOCARDIAL INJECTOR WITH SPRING LOADED PROTECTIVE ARRAY

(76) Inventor: Richard A. Schatz, San Diego, CA (US)

( * ) Notice: Subject to any disclaimer, the term of this patent is extended or adjusted under 35 U.S.C. 154(b) by 280 days.

(21) Appl. No.: 12/940,800

(22) Filed: Nov. 5, 2010

(65) Prior Publication Data

US 2011/0054444 A1    Mar. 3, 2011

Related U.S. Application Data

(62) Division of application No. 12/359,812, filed on Jan. 26, 2009.

(51) Int. Cl.
*A61M 25/09* (2006.01)

(52) U.S. Cl.
USPC .......................................... 604/509; 604/510

(58) Field of Classification Search .................. 604/509, 604/510, 164.01–164.13, 165.01
See application file for complete search history.

(56) References Cited

U.S. PATENT DOCUMENTS

| | | | |
|---|---|---|---|
| 5,312,341 A * | 5/1994 | Turi | 604/103.05 |
| 5,713,874 A * | 2/1998 | Ferber | 604/198 |
| 5,882,340 A * | 3/1999 | Yoon | 604/164.12 |
| 6,203,533 B1 * | 3/2001 | Ouchi | 604/264 |
| 6,408,203 B2 * | 6/2002 | Mackin | 600/433 |
| 6,582,400 B1 * | 6/2003 | Hawk et al. | 604/164.01 |
| 6,767,338 B2 * | 7/2004 | Hawk et al. | 604/164.01 |
| 6,835,193 B2 * | 12/2004 | Epstein et al. | 604/507 |
| 2003/0028172 A1 * | 2/2003 | Epstein et al. | 604/507 |
| 2007/0282267 A1 * | 12/2007 | Schatz | 604/164.01 |
| 2008/0004569 A1 * | 1/2008 | McCrystle et al. | 604/104 |
| 2008/0086110 A1 * | 4/2008 | Galdonik et al. | 604/509 |

* cited by examiner

*Primary Examiner* — Kevin C. Sirmons
*Assistant Examiner* — Michael J Anderson
(74) *Attorney, Agent, or Firm* — Nydegger & Associates

(57) ABSTRACT

A system is provided for performing injections in the ventricle of a patient. The system includes an injection catheter with a proximal and distal end. Importantly, a flexible array is mounted at the distal end of the injection catheter and is moveable between a protective configuration and a flared configuration. Also, a needle of variable length is mounted on the distal end of the injection catheter and is covered by the flexible array when the array is in its protective configuration. In order to manipulate the flexible array, a locking mechanism is mounted on the proximal end of the injection catheter for engagement with the flexible array. When selectively operated, the locking mechanism moves the array from its protective configuration to the flared configuration, holds the array in its flared configuration for an injection, and subsequently moves the array back to its protective configuration.

16 Claims, 2 Drawing Sheets

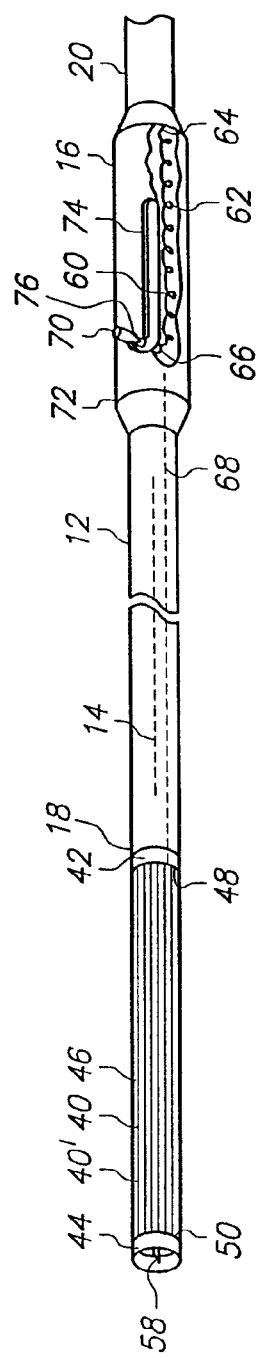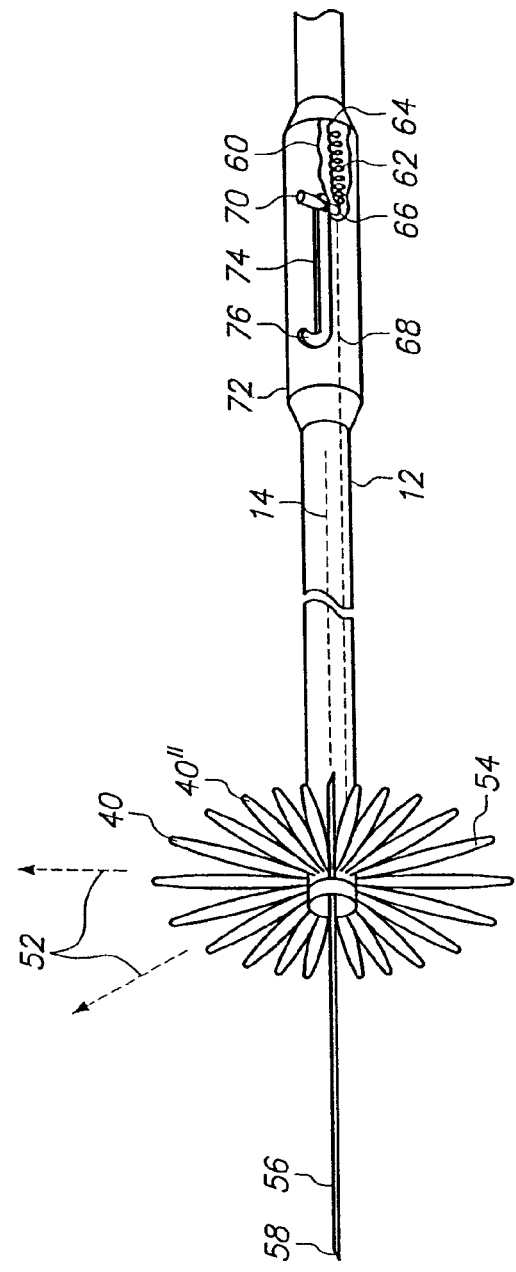

MYOCARDIAL INJECTOR WITH SPRING LOADED PROTECTIVE ARRAY

This application is a divisional of application Ser. No. 12/359,812, filed Jan. 26, 2009, which is currently pending. The contents of application Ser. No. 12/359,812 are incorporated herein by reference.

FIELD OF THE INVENTION

The present invention pertains generally to devices and methods for delivering medicaments to a patient. More specifically, the present invention pertains to devices and methods for performing intra myocardial injections. The present invention is particularly, but not exclusively, useful as a device and method for selectively protecting a needle tip as it is advanced to an intra myocardial injection site.

BACKGROUND OF THE INVENTION

Intravascular catheters are used in a wide variety of medical procedures by inserting the catheter into the vascular system of the patient at an easily accessible location. Thereafter, the tip of the catheter is advanced through the vasculature to a desired target site. In this manner, virtually any target site in the patient's vascular system may be remotely accessed. Of particular interest here are those medical procedures that require the use of injection catheters to inject therapeutic or diagnostic agents into various target tissues within the human body. When so used, an advantage of injection catheters is that the target tissue may be accessed by minimally invasive surgical techniques.

In many applications the target tissue is within a wall of an organ, such as the heart. For instance, therapeutic or diagnostic agents such as genes, proteins, drugs, plasmids, vectors, stem cells, skeletal myoblasts or any cell therapy may be injected directly into the heart. When the target tissue is within the wall of an organ, however, it is often desirable to inject the therapeutic or diagnostic agent into the tissue proximate the center of the organ wall. In these applications, if the needle of the injection catheter inadvertently passes through the wall, the therapeutic or diagnostic agents that are dispensed from the distal end of the needle will not be effectively delivered to the target tissue. Further, because the injection procedure often requires the thrust of a needle in the distal direction, the required motion can cause the catheter itself to contact and perforate or otherwise injure the wall of the organ which can be fatal. Further, it must be ensured that the needle tip does not perforate or damage the aortic and mitral valve apparatus and the chordate tendineae as the injection catheter is advanced to the injection site.

In light of the above, it is an object of the present invention to provide a system and method that protects the aortic and mitral valve apparatus and the chordate tendineae from injury and perforation during advancement of an injection catheter to an intra myocardial injection site. Still another object of the invention is to provide a device and method for performing an intra myocardial injection from a catheter in which a retractable barrier prevents contact between the catheter and the myocardial tissue and allows the physician to advance the needle with confidence and without fear of perforating the myocardial tissue with the catheter. Still another object of the present invention is to provide a system for performing an intra myocardial injection by a single operator that does not require the operator to disengage his hands during the procedure. Yet another object of the present invention is to provide a device and method for performing intra myocardial injections which is easy to implement, simple to perform, and cost effective.

SUMMARY OF THE INVENTION

In accordance with the present invention, an injection system is provided to perform intra myocardial injections, including transvalvular (aortic) or epicardial injections in the left ventricle, or injections in the right ventricle, while preventing unnecessary trauma to ventricle structures or to adjacent myocardial tissue. Structurally, the injection system includes an injection catheter that has a proximal end and distal end and defines a longitudinal axis.

Along the axis, the injection catheter is provided with a needle that extends from the distal end of the catheter to a tip. Further, the system provides a flexible array mounted at the distal end of the injection catheter. Specifically, the array includes a proximal ring member that is fixedly attached to the distal end of the injection catheter. Also, the array includes a distal non-fixed, sliding ring member which may be moved axially relative to the proximal ring member. Importantly, a plurality of wires interconnects the two ring members.

In a protective configuration, the array is substantially cylindrical shaped and is aligned with the axis of the injection catheter. In this configuration, the wires are substantially linear and the distal ring member extends distally beyond or at the needle tip. In a flared configuration, the array is substantially disk-shaped and lies in a plane substantially perpendicular to the axis. Further, each wire is biased to form a loop in the perpendicular plane when the proximal ring member is juxtaposed with the sliding distal ring member to establish the flared configuration.

In order to move the array between the protective and flared configurations, the distal ring member is connected to a locking mechanism. Structurally, the locking mechanism includes a contraction spring interconnected between the distal ring member and the proximal end of the injection catheter. Further, a lever is interconnected to the distal end of the spring. In order to control movement of the lever, it is positioned through a guide slot formed in a housing holding the spring. Importantly, the slot forms a notch for holding the lever against the contraction forces of the spring.

In order to safely advance the injection catheter to an injection site, the lever is moved axially toward the needle tip to stretch the contraction spring. As a result, the array moves from the flared configuration to the protective configuration. When the array is in the protective configuration, it covers the needle. Further, when the array is in the protective configuration, the lever is received and held in the notch of the slot.

After the injection catheter is advanced to the injection site, the lever is released from the notch, and the spring pulls the lever axially away from the needle tip. As a result, the array is pulled back into the flared configuration and the needle tip is exposed. With this arrangement, the needle may be advanced to perform an injection while the flared array abuts and protects the tissue adjacent the injection site.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 2A is a side view of the injection catheter of FIG. 1, shown with its array in a protected configuration in accordance with the present invention; and FIG. 2B is a side view of the injection catheter of FIG. 2A, shown with its array in a flared configuration in accordance with the present invention.

DESCRIPTION OF THE PREFERRED EMBODIMENTS

Figure 1:
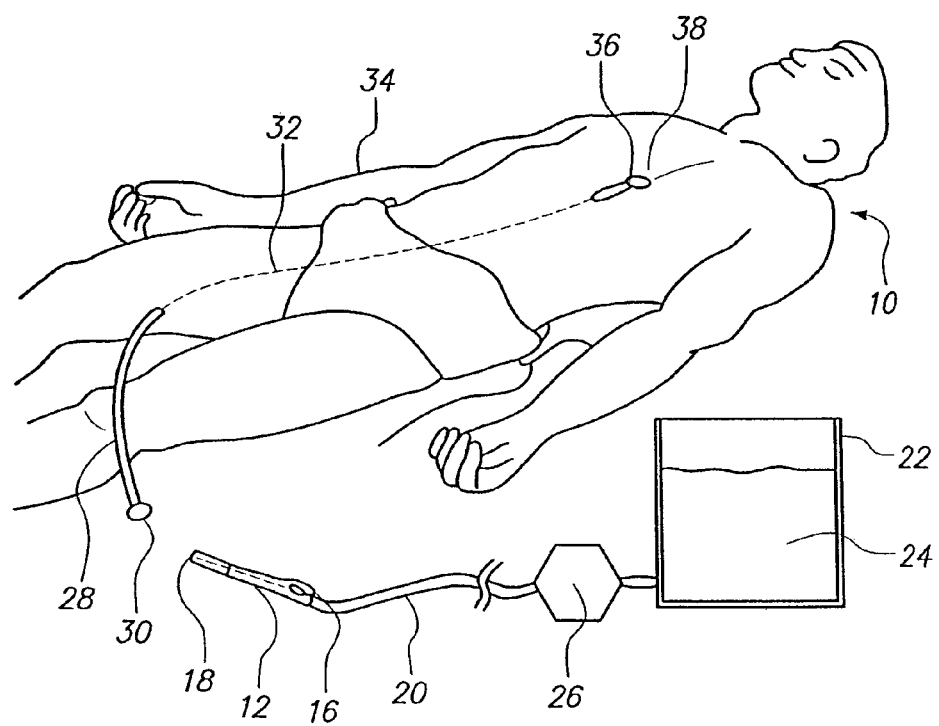
FIG. 1 is a perspective view of an environment wherein an injection system for performing an injection in a patient is being used in accordance with the present invention.

Referring initially to FIG. 1, an intra myocardial injection system in accordance with the present invention is shown, and is generally designated 10. As shown in FIG. 1, the injection system 10 includes an injection catheter 12 that extends along an axis 14 (shown in FIG. 2A) from a proximal end 16 to a distal end 18. As is shown, the proximal end 16 of the injection catheter 12 is connected to tubing 20. For purposes of the present invention, the tubing 20 is in fluid communication with a vessel 22 for holding medicament 24 or other fluid for medical treatment. Also, a syringe 26 is provided for moving the fluid medicament 24 injection catheter 12 for an injection. As further shown, a guiding catheter 28 forming a lumen 30 is positioned in the vasculature 32 of a patient 34. Specifically, the guiding catheter 28 leads to an injection site 36, retrograde across the aortic valve into the left ventricular chamber, surrounded by adjacent myocardial tissue 38.

Referring now to FIG. 2A, the structure of the injection catheter 12 may be understood. As shown, a flexible array 40 is mounted at the distal end 18 of the injection catheter 12. Structurally, the array 40 includes a proximal ring member 42 fixedly attached to the distal end 18 of the injection catheter 12. Further, the array 40 includes a distal ring member 44 that is moveable along the axis 14 relative to the proximal ring member 42. Also, the flexible array 40 includes a plurality of wires 46 that interconnect the ring members 42, 44. As shown, each wire 46 has an end 48 affixed to the proximal ring member 42 and an end 50 affixed to the distal ring member 44. In certain embodiments, the wires 46 may comprise stainless steel, nitinol, cobalt chromium or other desired materials.

In FIG. 2A, the flexible array 40 is shown in a protective configuration 40' in which array 40 is substantially cylindrical shaped and is aligned with the axis 14 of the injection catheter 12. However, the array 40 is selectively moveable to a flared configuration 40" shown in FIG. 2B. In the flared configuration 40", the array 40 is substantially disk-shaped and lies in a plane 52 substantially perpendicular to the axis 14. For purposes of the present invention, each wire 46 is biased to form a loop 54 in the perpendicular plane 52 when the proximal ring member 42 is juxtaposed with the distal ring member 44 to establish the flared configuration 40".

As shown in FIGS. 2A and 2B, the injection system 10 further includes a needle 56 that has a distal tip 58. Importantly, the needle tip 58 is covered by the flexible array 40 when the array 40 is in its protective configuration 40' in FIG. 2A. When the flexible array 40 is in its flared configuration 40" in FIG. 2B, the needle tip 58 is exposed to perform an injection.

In order to move the array 40 between its configurations 40', 40", the injection system 10 includes a locking mechanism 60. As shown in FIGS. 2A and 2B, the locking mechanism 60 is mounted on the proximal end 16 of the injection catheter 12 and engages the flexible array 40 at the distal end 18. Structurally, the locking mechanism 60 includes a contraction spring 62 with an end 64 attached to the proximal end 16 of the injection catheter 12. Further, the spring 62 has an end 66 connected to the distal ring member 44 of the flexible array 40 via a connection arm 68 (shown in phantom).

Also, the mechanism 60 provides a push-button lever 70 that is interconnected to the end 66 of the spring 62. As shown, the injection system 10 provides a housing 72 at the proximal end 16 of the catheter 12 for holding the spring 62. Further, the housing 72 forms a slot 74 that limits movement of the lever 70. Importantly, the slot 74 includes a notch 76 that holds the lever 70 against axial movement as described below.

For the injection system 10, the spring 62 is biased toward the position shown in FIG. 2B. As a result, the array 40 is biased towards its flared configuration 40". For operation, the lever 70 is moved axially from its position in FIG. 2B to its position shown in FIG. 2A. In FIG. 2A, the lever 70 rests in notch 76 against the contraction force of the spring 62. As can be seen from FIGS. 2A and 2B, the array 40 is extending from its flared configuration 40" to its protective configuration 40' when the lever 70 is pushed into the notch 76. When the needle tip 58 is protected, the injection catheter 12 may be advanced through the guiding catheter 28 (shown in FIG. 1) to the injection site 36. After the injection catheter 12 is positioned at the injection site 36, the lever 70 is released from the notch 76 and the spring 62 pulls the distal ring member 44 to position the array 40 in the flared configuration 40". As a result, the array 40 abuts the myocardial wall of the patient 34. Importantly, the array 40 may have a high friction surface for gripping the wall trabeculae. Additionally or alternatively, the array 40 may include tines for gripping the wall trabeculae. After the array 40 grips the myocardial wall, the needle tip 58 may be advanced into the injection site 36 to perform the injection while the array 40 prevents the catheter 12 from perforating or otherwise damaging the adjacent tissue 38. After the injection is performed, the lever 70 is again advanced so that the array 40 is in its protective configuration 40' and the injection catheter 12 is removed from the patient 34, or easily maneuvered for multiple injection sites.

In FIG. 2B, the needle 56 has an exposed length from its tip 58 to the distal ring member 44 (as shown in FIG. 2A). In certain embodiments, this length is designed to be less than the thickness of a myocardial wall. As a result, there is no danger of the needle tip 58 passing completely through the myocardial wall. Therefore, a successful myocardial injection is facilitated due to the predetermined exposed length of the needle 56. In certain embodiments, the needle length may be variable using a screw-type mechanism, or a variety of needles having varied fixed lengths (3-6 mm) may be provided.

While the particular Myocardial Injector with Spring Loaded Protective Array as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for performing injections in the myocardial wall of a patient which comprises the steps of:
    providing an intra myocardial injector including (a) an injection catheter having a proximal end and a distal end, and defining a longitudinal axis, (b) a flexible array mounted at the distal end of the injection catheter, with the array being moveable between a protective configuration wherein the array is substantially cylindrical shaped and is aligned with the axis of the injection catheter, and a flared configuration wherein the array is substantially disk-shaped and lies in a plane substantially perpendicular to the axis, (c) a needle mounted on the distal end of the injection catheter and covered by the flexible array when the array is in its protective configuration, and (d) a locking mechanism mounted on the proximal end of the injection catheter for engagement with the flexible array at the distal end of the injection catheter, wherein the locking mechanism includes a spring biasing the array into a flared configuration to abut against tissue during an injection and is selectively manipulable to release the array from a locked, protective configuration to its flared configuration, and to thereafter hold the array in its flared configuration for an injection and to subsequently move the flexible array from its flared configuration to its protective configuration;

positioning a guiding catheter in the ventricle of the patient;

moving the flexible array to the protective configuration;

advancing the injection catheter through a lumen in the guiding catheter to an injection site;

releasing the flexible array from its protective configuration to its flared configuration;

performing an injection with the needle while the flexible array is flared to prevent contact between the injection catheter and the myocardial tissue during the injection; and returning the flexible array to its protective configuration for removal from the vasculature.

2. A method as recited in claim 1 wherein the flexible array comprises;

a proximal ring member fixedly attached to the distal end of the injection catheter;

a distal ring member moveable along the axis relative to the proximal ring member; and a plurality of wires, wherein each wire has a first end affixed to the distal ring member and a second end affixed to the proximal ring member, and wherein each wire is biased to form a loop in the perpendicular plane when the proximal ring member is juxtaposed with the distal ring member to establish the flared configuration for the array.

3. A method as recited in claim 2 wherein:

the spring has a first end attached to the injection catheter at the proximal end of the injection catheter and a second end attached to the distal ring member of the flexible array, wherein the spring is relaxed when the array is in its flared configuration; and the locking mechanism further comprises;

a push-button lever for alternatively advancing the distal ring member to stretch the spring and establish the flexible array in its protective configuration, and for thereafter releasing the distal ring member for a return of the flexible array to its flared configuration under the influence of the spring.

4. A method as recited in claim 3 wherein the injector further comprises a housing for holding the spring, wherein said housing forms a slot that limits axial movement of the lever, wherein the slot includes a notch for holding the lever when the flexible array is in its protective configuration.

5. A method as recited in claim 4 wherein the injector further comprises:

a source of a fluid medicament, wherein the fluid source is connected in fluid communication with the needle; and a syringe for moving fluid medicament through the needle for an injection when the flexible array is in its flared configuration.

6. A method for performing injections into the myocardial wall of a patient which comprises the steps of:

positioning an injection catheter proximate an injection site on the myocardial wall, wherein the injection catheter defines an axis;

reconfiguring a flexible array mounted at the distal end of the injection catheter by unlocking the array from a protective configuration, wherein the array is substantially cylindrical shaped and is aligned with the axis of the injection catheter to cover a needle mounted on the distal end of the injection catheter, and using a spring to bias the array into a flared configuration wherein the array is substantially disk-shaped and lies in a plane substantially perpendicular to the axis, to expose the needle;

advancing the exposed needle into myocardial tissue of the wall to perform an injection, while the flexible array is in its flared configuration to abut the array against tissue and prevent contact between the injection catheter and the myocardial tissue during the injection; and withdrawing the needle from the myocardial tissue after the injection.

7. A method as recited in claim 6 further comprising the steps of:

locating a guiding catheter in the ventricle of the patient;

moving the flexible array to the protective configuration; and moving the injection catheter through a lumen in the guiding catheter to the injection site.

8. A method as recited in claim 6 wherein the spring is connected between the injection catheter and the flexible array with the spring being relaxed when the array is in its flared configuration, and wherein the reconfiguring step further comprises the steps of;

stretching the spring to establish the flexible array in its protective configuration; and subsequently releasing the flexible array for a return to its flared configuration under the influence of the spring.

9. A method as recited in claim 7 further comprising the step of locking the array in its protective configuration upon conclusion of the stretching step for a subsequent quick-release of the array from the protective configuration and into the flared configuration during the releasing step.

10. A method as recited in claim 6 wherein the flexible array comprises:

a proximal ring member fixedly attached to the distal end of the injection catheter;

a distal ring member moveable along the axis relative to the proximal ring member; and a plurality of wires, wherein each wire has a first end affixed to the distal ring member and a second end affixed to the proximal ring member, and wherein each wire is biased to form a loop in the perpendicular plane when the proximal ring member is juxtaposed with the distal ring member to establish the flared configuration for the array.

11. A method for performing injections in the myocardial wall of a patient which comprises the steps of:

unlocking a flexible array from a protective configuration wherein the array is substantially cylindrical shaped and is aligned with the axis of the injection catheter to cover the needle with the flexible array when the array is in its protective configuration;

using a spring to bias the array into a flared configuration to abut against tissue during an injection, wherein the flexible array is mounted on a distal end of an injection catheter, wherein the injection catheter defines an axis and the flexible array is substantially disk-shaped and lies in a plane substantially perpendicular to the axis to expose a needle when the flexible array is in the flared configuration;

advancing the needle into myocardial tissue to perform an injection, while the flexible array is in its flared configuration to prevent contact between the injection catheter and the myocardial tissue during the injection;

withdrawing the needle from the myocardial tissue after the injection; and reconfiguring the flexible array into the protective configuration.

12. A method as recited in claim 11 further comprising the steps of:

pre-positioning a guiding catheter in the ventricle of the patient; and advancing the injection catheter through a lumen in the guiding catheter to an injection site while the flexible array is in its protective configuration.

13. A method as recited in claim 11 wherein the spring is connected between the injection catheter and the flexible array with the spring being relaxed when the array is in its flared configuration, and wherein the reconfiguring step is accomplished by stretching the spring to establish the flexible array in its protective configuration.

14. A method as recited in claim 13 further comprising the step of locking the array in its protective configuration at a conclusion of the stretching step for a subsequent quick-release therefrom during the releasing step.

15. A method as recited in claim 13 wherein the establishing step is accomplished by releasing the flexible array from the protective configuration for a return to its flared configuration under the influence of the spring.

16. A method as recited in claim 11 wherein the flexible array comprises;

a proximal ring member fixedly attached to the distal end of the injection catheter;

a distal ring member moveable along the axis relative to the proximal ring member; and a plurality of wires wherein each wire has a first end affixed to the distal ring member and a second end affixed to the proximal ring member, and wherein each wire is biased to form a loop in the perpendicular plane when the proximal ring member is juxtaposed with the distal ring member to establish the flared configuration for the array.

* * * * *